(12) United States Patent
Jaroch et al.

(10) Patent No.: US 12,377,245 B2
(45) Date of Patent: Aug. 5, 2025

(54) METHOD OF DELIVERING A THERAPEUTIC AGENT TO A SOLID TUMOR FOR TREATMENT

(71) Applicant: TriSalus Life Sciences, Inc., Westminster, CO (US)

(72) Inventors: David Benjamin Jaroch, Arvada, CO (US); James E. Chomas, Denver, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 0 days.

(21) Appl. No.: 17/376,115

(22) Filed: Jul. 14, 2021

(65) Prior Publication Data

US 2021/0338976 A1    Nov. 4, 2021

Related U.S. Application Data

(60) Continuation of application No. 16/219,738, filed on Dec. 13, 2018, now Pat. No. 11,090,460, which is a (Continued)

(51) Int. Cl.
*A61M 25/00*     (2006.01)
*A61L 29/04*     (2006.01)
(Continued)

(52) U.S. Cl.
CPC ....... *A61M 25/0029* (2013.01); *A61L 29/041* (2013.01); *A61L 29/06* (2013.01); *A61L 29/08* (2013.01); *A61L 29/085* (2013.01); *A61L 29/145* (2013.01); *A61L 29/16* (2013.01); *A61M 25/04* (2013.01); *A61M 25/10* (2013.01); *A61F 2/013* (2013.01); *A61L 2300/426* (2013.01);
(Continued)

(58) Field of Classification Search
CPC .......... A61M 25/0029; A61M 25/0045; A61M 25/0023; A61M 25/0021; A61L 29/08; A61L 29/085

See application file for complete search history.

(56) References Cited

U.S. PATENT DOCUMENTS 4,261,341 A    4/1981  Hakim
4,311,587 A    1/1982  Nose
(Continued)

FOREIGN PATENT DOCUMENTS

CN    101449987 A    6/2009
CN    103260547 A    8/2013
(Continued)

OTHER PUBLICATIONS

US 7,169,126 B2, 01/2007, Zadno-Azizi (withdrawn)
(Continued)

*Primary Examiner* — Tasnim Mehjabin Ahmed
(74) *Attorney, Agent, or Firm* — Wan Chieh Lee; Trenton D. Hatherill; Haug Partners LLP

(57) ABSTRACT

A method for delivering a therapeutic agent to a tumor through a target vessel includes delivering the therapeutic agent through a lumen of a catheter which has been coated or otherwise structured to reduce the wall shear stress during delivery of the immunotherapy and by generating turbulent flow during the delivery of the therapeutic agent.

11 Claims, 4 Drawing Sheets

Related U.S. Application Data division of application No. 15/064,158, filed on Mar. 8, 2016, now abandoned.

(60) Provisional application No. 62/140,651, filed on Mar. 31, 2015.

(51) Int. Cl.

| *A61L 29/06* | (2006.01) |
| *A61L 29/08* | (2006.01) |
| *A61L 29/14* | (2006.01) |
| *A61L 29/16* | (2006.01) |
| *A61M 25/04* | (2006.01) |
| *A61M 25/10* | (2013.01) |
| *A61F 2/01* | (2006.01) |

(52) U.S. Cl.
CPC ..... *A61L 2300/608* (2013.01); *A61L 2400/10* (2013.01); *A61L 2420/02* (2013.01); *A61L 2420/08* (2013.01); *A61M 2025/0004* (2013.01); *A61M 2025/0042* (2013.01); *A61M 2025/0047* (2013.01); *A61M 2025/105* (2013.01); *A61M 2025/1052* (2013.01); *A61M 2202/0007* (2013.01)

(56) References Cited

U.S. PATENT DOCUMENTS

| | | |
|---|---|---|
| 4,655,771 A | 4/1987 | Wallsten |
| 4,714,460 A | 12/1987 | Calderon |
| 4,738,740 A | 4/1988 | Pinchuk et al. |
| 4,800,016 A | 1/1989 | Yang |
| 4,840,542 A | 6/1989 | Abbott |
| 4,883,459 A | 11/1989 | Calderon |
| 4,892,518 A | 1/1990 | Cupp |
| 5,024,668 A | 6/1991 | Peters et al. |
| 5,030,199 A | 7/1991 | Barwick |
| 5,071,407 A | 12/1991 | Termin |
| 5,084,015 A | 1/1992 | Moriuchi |
| 5,171,299 A | 12/1992 | Heitzmann |
| 5,234,425 A | 8/1993 | Fogarty |
| 5,397,307 A | 3/1995 | Goodin |
| 5,397,308 A | 3/1995 | Ellis |
| 5,411,478 A | 5/1995 | Stillabower |
| 5,419,763 A | 5/1995 | Hildebrand |
| 5,484,399 A | 1/1996 | Diresta |
| 5,484,412 A | 1/1996 | Pierpont |
| 5,496,277 A | 3/1996 | Termin |
| 5,607,466 A | 3/1997 | Imbert |
| 5,668,237 A | 9/1997 | Popall |
| 5,688,237 A | 11/1997 | Rozga |
| 5,725,571 A | 3/1998 | Mbert |
| 5,755,687 A | 5/1998 | Donlon |
| 5,755,769 A | 5/1998 | Richard |
| 5,759,205 A | 6/1998 | Valentini |
| 5,810,789 A | 9/1998 | Powers |
| 5,836,905 A | 11/1998 | Lemelson |
| 5,836,967 A | 11/1998 | Schneider |
| 5,893,869 A | 4/1999 | Barnhart |
| 5,895,399 A | 4/1999 | Barbut |
| 5,897,567 A | 4/1999 | Ressemann |
| 5,910,154 A | 6/1999 | Tsugita |
| 5,911,734 A | 6/1999 | Tsugita |
| 5,954,745 A | 9/1999 | Gertler et al. |
| 5,957,974 A | 9/1999 | Thompson |
| 5,989,281 A | 11/1999 | Barbut et al. |
| 6,001,118 A | 12/1999 | Daniel |
| 6,010,522 A | 1/2000 | Barbut |
| 6,027,520 A | 2/2000 | Tsugita |
| 6,042,598 A | 3/2000 | Tsugita |
| 6,051,014 A | 4/2000 | Jang |
| 6,059,745 A | 5/2000 | Gelbfish |
| 6,152,946 A | 11/2000 | Broome |
| 6,165,199 A | 12/2000 | Barbut |
| 6,165,200 A | 12/2000 | Tsugita |
| 6,168,579 B1 | 1/2001 | Tsugita |
| 6,179,851 B1 | 1/2001 | Barbut |
| 6,231,551 B1 | 5/2001 | Barbut |
| 6,235,044 B1 | 5/2001 | Root |
| 6,258,120 B1 | 7/2001 | McKenzie |
| 6,306,074 B1 | 10/2001 | Waksman |
| 6,306,163 B1 | 10/2001 | Fitz |
| 6,309,399 B1 | 10/2001 | Barbut |
| 6,361,545 B1 | 3/2002 | Macoviak |
| 6,364,895 B1 | 4/2002 | Greenhalgh |
| 6,371,969 B1 | 4/2002 | Tsugita |
| 6,371,971 B1 | 4/2002 | Tsugita |
| 6,375,670 B1 | 4/2002 | Greenhalgh |
| 6,383,206 B1 | 5/2002 | Gillick |
| 6,395,014 B1 | 5/2002 | Macoviak |
| 6,416,495 B1 | 7/2002 | Kriesel |
| 6,436,112 B2 | 8/2002 | Wensel |
| 6,443,926 B1 | 9/2002 | Kletschka |
| 6,478,783 B1 | 11/2002 | Moorehead |
| 6,485,456 B1 | 11/2002 | Kletschka |
| 6,485,502 B2 | 11/2002 | Don Michael |
| 6,499,487 B1 | 12/2002 | McKenzie |
| 6,500,203 B1 | 12/2002 | Thompson |
| 6,520,183 B2 | 2/2003 | Amar |
| 6,530,935 B2 | 3/2003 | Wensel |
| 6,533,800 B1 | 3/2003 | Barbut |
| 6,537,294 B1 | 3/2003 | Boyle |
| 6,537,297 B2 | 3/2003 | Tsugita |
| 6,540,722 B1 | 4/2003 | Boyle |
| 6,551,303 B1 | 4/2003 | Van Tassel |
| 6,565,552 B1 | 5/2003 | Barbut |
| 6,569,146 B1 | 5/2003 | Werner |
| 6,582,396 B1 | 6/2003 | Parodi |
| 6,589,264 B1 | 7/2003 | Barbut |
| 6,592,546 B1 | 7/2003 | Barbut |
| 6,607,506 B2 | 8/2003 | Kletschka |
| 6,620,148 B1 | 9/2003 | Tsugita |
| 6,635,070 B2 | 10/2003 | Leeflang |
| 6,641,553 B1 | 11/2003 | Chee |
| 6,641,572 B2 | 11/2003 | Cherkassky |
| 6,645,220 B1 | 11/2003 | Huter |
| 6,645,222 B1 | 11/2003 | Parodi |
| 6,645,223 B2 | 11/2003 | Boyle |
| 6,652,555 B1 | 11/2003 | VanTassel |
| 6,652,556 B1 | 11/2003 | VanTassel |
| 6,656,351 B2 | 12/2003 | Boyle |
| 6,673,090 B2 | 1/2004 | Root |
| 6,676,682 B1 | 1/2004 | Tsugita |
| 6,689,150 B1 | 2/2004 | VanTassel |
| 6,692,508 B2 | 2/2004 | Wensel |
| 6,692,509 B2 | 2/2004 | Wensel |
| 6,692,513 B2 | 2/2004 | Streeter |
| 6,695,813 B1 | 2/2004 | Boyle |
| 6,695,858 B1 | 2/2004 | Dubrul |
| 6,699,231 B1 | 3/2004 | Sterman |
| 6,702,834 B1 | 3/2004 | Boylan |
| 6,706,053 B1 | 3/2004 | Boylan |
| 6,706,055 B2 | 3/2004 | Douk |
| 6,730,108 B2 | 5/2004 | VanTassel |
| 6,743,196 B2 | 6/2004 | Barbut |
| 6,746,469 B2 | 6/2004 | Mouw |
| 6,746,489 B2 | 6/2004 | Dua |
| 6,802,317 B2 | 10/2004 | Goebel |
| 6,818,006 B2 | 11/2004 | Douk |
| 6,830,579 B2 | 12/2004 | Barbut |
| 6,837,898 B2 | 1/2005 | Boyle |
| 6,855,154 B2 | 2/2005 | Abdel-Gawwad |
| 6,866,677 B2 | 3/2005 | Douk |
| 6,887,258 B2 | 5/2005 | Denison |
| 6,896,690 B1 | 5/2005 | Lambrecht |
| 6,902,540 B2 | 6/2005 | Dorros |
| 6,908,474 B2 | 6/2005 | Hogendijk |
| 6,911,036 B2 | 6/2005 | Douk |
| 6,936,060 B2 | 8/2005 | Hogendijk |
| 6,939,362 B2 | 9/2005 | Boyle |
| 6,958,059 B2 | 10/2005 | Zadno-Azizi |
| 6,964,670 B1 | 11/2005 | Shah |
| 6,964,673 B2 | 11/2005 | Tsugita |

(56) References Cited

U.S. PATENT DOCUMENTS

| | | |
|---|---|---|
| 6,974,469 B2 | 12/2005 | Broome |
| 6,989,027 B2 | 1/2006 | Allen |
| 6,997,898 B2 | 2/2006 | Forman |
| 7,044,958 B2 | 5/2006 | Douk |
| 7,044,966 B2 | 5/2006 | Svanidze |
| 7,066,946 B2 | 6/2006 | Douk |
| 7,101,396 B2 | 9/2006 | Artof |
| 7,118,600 B2 | 10/2006 | Dua |
| 7,162,303 B2 | 1/2007 | Levin |
| 7,169,164 B2 | 1/2007 | Borillo |
| 7,172,614 B2 | 2/2007 | Boyle |
| 7,172,621 B2 | 2/2007 | Theron |
| 7,214,237 B2 | 5/2007 | Don Michael |
| 7,217,255 B2 | 5/2007 | Boyle |
| 7,223,253 B2 | 5/2007 | Hogendijk |
| 7,232,452 B2 | 6/2007 | Adams |
| 7,232,453 B2 | 6/2007 | Shimon |
| 7,241,304 B2 | 7/2007 | Boyle |
| 7,250,041 B2 | 7/2007 | Chiu |
| 7,252,675 B2 | 8/2007 | Denison |
| 7,279,000 B2 | 10/2007 | Cartier |
| 7,306,575 B2 | 12/2007 | Barbut |
| 7,322,957 B2 | 1/2008 | Kletschka |
| 7,326,226 B2 | 2/2008 | Root |
| 7,331,973 B2 | 2/2008 | Gesswein |
| 7,338,510 B2 | 3/2008 | Boylan |
| 7,344,549 B2 | 3/2008 | Boyle |
| 7,364,566 B2 | 4/2008 | Elkins |
| 7,371,249 B2 | 5/2008 | Douk |
| 7,425,215 B2 | 9/2008 | Boyle |
| 7,503,904 B2 | 3/2009 | Choi |
| 7,537,600 B2 | 5/2009 | Eskuri |
| 7,544,202 B2 | 6/2009 | Cartier |
| 7,572,272 B2 | 8/2009 | Denison |
| 7,582,100 B2 | 9/2009 | Johnson |
| 7,585,309 B2 | 9/2009 | Larson |
| 7,591,832 B2 | 9/2009 | Eversull |
| 7,604,650 B2 | 10/2009 | Bergheim |
| 7,647,115 B2 | 1/2010 | Levin |
| 7,653,438 B2 | 1/2010 | Deem |
| 7,658,747 B2 | 2/2010 | Forde |
| 7,686,781 B2 | 3/2010 | Vinten-Johansen |
| 7,780,696 B2 | 8/2010 | Daniel et al. |
| 7,833,242 B2 | 11/2010 | Gilson |
| 7,842,084 B2 | 11/2010 | Bicer |
| 7,846,139 B2 | 12/2010 | Zinn |
| 7,853,333 B2 | 12/2010 | Demarais |
| 7,873,417 B2 | 1/2011 | Demarais |
| 7,922,691 B2 | 4/2011 | Kletchka |
| 7,935,075 B2 | 5/2011 | Tockman |
| 7,937,143 B2 | 5/2011 | Demarais |
| 7,938,799 B2 | 5/2011 | Epstein |
| 7,993,324 B2 | 8/2011 | Barbut |
| 8,162,879 B2 | 4/2012 | Hattangadi |
| 8,172,792 B2 | 5/2012 | Wang |
| 8,182,446 B2 | 5/2012 | Schaeffer |
| 8,200,312 B2 | 6/2012 | Degani |
| 8,251,948 B2 | 8/2012 | Goldman |
| 8,257,384 B2 | 9/2012 | Bates |
| 8,262,611 B2 | 9/2012 | Teesllink |
| 8,397,578 B2 | 3/2013 | Miesel |
| 8,409,166 B2 | 4/2013 | Wiener |
| 8,500,775 B2 | 8/2013 | Chomas |
| 8,696,698 B2 | 4/2014 | Chomas |
| 8,696,699 B2 | 4/2014 | Chomas |
| 8,821,476 B2 | 9/2014 | Agah |
| 8,852,207 B2 | 10/2014 | Simpson |
| 8,945,116 B2 | 2/2015 | MacAdam et al. |
| 8,951,280 B2 | 2/2015 | Cohn et al. |
| 9,023,010 B2 | 5/2015 | Chiu |
| 9,061,117 B2 | 6/2015 | Roberts |
| 9,078,982 B2 | 7/2015 | Lane |
| 9,089,341 B2 | 7/2015 | Chomas |
| 9,107,734 B2 | 8/2015 | Belson |
| 9,126,016 B2 | 9/2015 | Chomas |
| 9,174,020 B2 | 11/2015 | Allen |
| 9,205,226 B2 | 12/2015 | Allen |
| 9,265,914 B2 | 2/2016 | Fulton, III |
| 9,345,499 B2 | 5/2016 | Strauss |
| 9,364,358 B2 | 6/2016 | Cohen |
| 9,457,171 B2 | 10/2016 | Agah |
| 9,463,304 B2 | 10/2016 | Agah |
| 9,474,533 B2 | 10/2016 | Mathis |
| 9,539,081 B2 | 1/2017 | Chomas |
| 9,550,046 B1 | 1/2017 | Allen |
| 9,597,480 B2 | 3/2017 | Purdy |
| 9,604,037 B2 | 3/2017 | Fischer, Jr. |
| 9,737,693 B2 | 8/2017 | Helkowski |
| 9,770,319 B2 | 9/2017 | Pinchuk |
| 9,808,332 B2 | 11/2017 | Chomas |
| 9,844,383 B2 | 12/2017 | Allen |
| 9,913,959 B2 | 3/2018 | Purdy |
| 9,968,740 B2 | 5/2018 | Pinchuk |
| 10,076,404 B2 | 9/2018 | Bonnette |
| 10,092,742 B2 | 10/2018 | Genstler |
| 10,099,040 B2 | 10/2018 | Agah |
| 10,130,762 B2 | 11/2018 | Allen |
| 11,090,460 B2 * | 8/2021 | Jaroch ............ A61L 29/085 |
| 11,324,619 B1 | 5/2022 | Yacoby |
| 2001/0041862 A1 | 11/2001 | Glickman |
| 2002/0042593 A1 | 4/2002 | Mickley |
| 2002/0161390 A1 | 10/2002 | Mouw |
| 2002/0161394 A1 | 10/2002 | Macoviak |
| 2003/0097114 A1 | 5/2003 | Ouriel |
| 2003/0125790 A1 | 7/2003 | Fastovsky |
| 2003/0187474 A1 | 10/2003 | Keegan |
| 2003/0212361 A1 | 11/2003 | Boyle |
| 2003/0233115 A1 | 12/2003 | Eversull |
| 2004/0006305 A1 | 1/2004 | Hebert |
| 2004/0054315 A1 | 3/2004 | Levin |
| 2004/0068288 A1 | 4/2004 | Palmer |
| 2004/0143185 A1 | 7/2004 | Zatezalo |
| 2004/0215142 A1 | 10/2004 | Matheis |
| 2004/0220511 A1 * | 11/2004 | Scott ............ A61N 1/325<br>604/20 |
| 2004/0220521 A1 | 11/2004 | Barbut |
| 2004/0220609 A1 | 11/2004 | Douk |
| 2004/0225354 A1 | 11/2004 | Allen |
| 2004/0256584 A1 | 12/2004 | Zimmerling |
| 2004/0260333 A1 | 12/2004 | Dubral |
| 2005/0004517 A1 | 1/2005 | Courtney |
| 2005/0010285 A1 | 1/2005 | Lambrecht |
| 2005/0015048 A1 | 1/2005 | Chiu |
| 2005/0015112 A1 | 1/2005 | Cohn |
| 2005/0113798 A1 | 5/2005 | Slater |
| 2005/0119688 A1 | 6/2005 | Burgheim |
| 2005/0149112 A1 | 7/2005 | Barbut |
| 2005/0261759 A1 | 11/2005 | Lambrecht |
| 2006/0121012 A1 * | 6/2006 | Kutryk ............ A61L 29/103<br>623/1.46 |
| 2006/0124140 A1 | 6/2006 | Forsell |
| 2006/0167537 A1 | 7/2006 | Larsson |
| 2006/0173490 A1 | 8/2006 | Lafontaine |
| 2006/0177478 A1 | 8/2006 | Humes |
| 2006/0263301 A1 | 11/2006 | Vernon |
| 2006/0264898 A1 | 11/2006 | Beasley |
| 2007/0106258 A1 | 5/2007 | Chiu |
| 2007/0106324 A1 | 5/2007 | Gamer |
| 2007/0179590 A1 | 8/2007 | Lu |
| 2007/0225800 A1 * | 9/2007 | Sahatjian ............ A61F 2/91<br>623/1.42 |
| 2007/0239135 A9 | 10/2007 | Barbut |
| 2008/0031740 A1 | 2/2008 | Miyazaki |
| 2008/0031962 A1 | 2/2008 | Boyan |
| 2008/0033341 A1 | 2/2008 | Grad |
| 2008/0039786 A1 | 2/2008 | Epstein |
| 2008/0051758 A1 | 2/2008 | Rioux |
| 2008/0097273 A1 | 4/2008 | Levin |
| 2008/0103523 A1 | 5/2008 | Chiu |
| 2008/0147007 A1 | 6/2008 | Freyman |
| 2008/0234796 A1 | 9/2008 | Dorn |
| 2009/0018486 A1 | 1/2009 | Goren et al. |
| 2009/0018498 A1 | 1/2009 | Chiu |
| 2009/0076409 A1 | 3/2009 | Wu |

(56) References Cited

U.S. PATENT DOCUMENTS

| | | |
|---|---|---|
| 2009/0088676 A1 | 4/2009 | Murata |
| 2009/0198321 A1 | 8/2009 | Sutermeister |
| 2009/0222035 A1 | 9/2009 | Schneiderman |
| 2009/0234266 A1 | 9/2009 | Solomon |
| 2009/0234283 A1 | 9/2009 | Burton |
| 2009/0264819 A1 | 10/2009 | Diethrich |
| 2010/0015200 A1* | 1/2010 | McClain ............ A61L 27/34 424/94.1 |
| 2010/0168785 A1 | 7/2010 | Parker |
| 2010/0274277 A1 | 10/2010 | Eaton |
| 2010/0331815 A1 | 12/2010 | Alt |
| 2011/0046542 A1 | 2/2011 | Evans |
| 2011/0130657 A1 | 6/2011 | Chomas |
| 2011/0137399 A1 | 6/2011 | Chomas |
| 2011/0190698 A1* | 8/2011 | Consigny ............ A61M 25/10 604/103.01 |
| 2011/0218494 A1* | 9/2011 | Gerrans ........ A61B 17/320725 604/101.05 |
| 2011/0264057 A1* | 10/2011 | Eversull ............ C08J 7/043 156/443 |
| 2011/0288529 A1 | 11/2011 | Fulton |
| 2011/0295114 A1 | 12/2011 | Agah |
| 2011/0295203 A1 | 12/2011 | Hayes |
| 2012/0116351 A1* | 5/2012 | Chomas ............ A61M 25/0075 604/508 |
| 2012/0259206 A1 | 10/2012 | Roberts |
| 2013/0079731 A1 | 3/2013 | Chomas |
| 2013/0116655 A1 | 5/2013 | Bacino |
| 2013/0226166 A1 | 8/2013 | Chomas |
| 2014/0066830 A1 | 3/2014 | Lad |
| 2014/0073536 A1 | 3/2014 | Lin |
| 2014/0207178 A1 | 7/2014 | Chomas |
| 2014/0276135 A1 | 9/2014 | Agah |
| 2014/0276411 A1 | 9/2014 | Cowan |
| 2014/0364835 A1 | 12/2014 | Allen |
| 2014/0378951 A1 | 12/2014 | Dye |
| 2015/0272716 A1 | 10/2015 | Pinchuk |
| 2015/0306311 A1 | 10/2015 | Pinchuk |
| 2016/0015508 A1 | 1/2016 | Chomas |
| 2016/0015948 A1 | 1/2016 | Agah |
| 2016/0074633 A1 | 3/2016 | Schaffner |
| 2016/0082178 A1 | 3/2016 | Agah |
| 2016/0235942 A1 | 8/2016 | Alt |
| 2016/0235950 A1 | 8/2016 | Murata |
| 2016/0249969 A1 | 9/2016 | Santoinanni |
| 2016/0256626 A9 | 9/2016 | Chomas |
| 2016/0310148 A1 | 10/2016 | Allen |
| 2017/0000493 A1 | 1/2017 | Boehm, Jr. |
| 2017/0049946 A1 | 2/2017 | Kapur |
| 2017/0056629 A1 | 3/2017 | Agah |
| 2017/0157370 A1 | 6/2017 | Agah |
| 2017/0173309 A1 | 6/2017 | Fischer, Jr. |
| 2017/0189654 A1 | 7/2017 | Schwartz |
| 2017/0209666 A1 | 7/2017 | Quigley |
| 2017/0319820 A1 | 11/2017 | Johnson |
| 2017/0368306 A1 | 12/2017 | Tal |
| 2018/0055620 A1 | 1/2018 | Chomas |
| 2018/0116522 A1 | 5/2018 | Brenneman |
| 2018/0125502 A1 | 5/2018 | Allen |
| 2018/0250469 A1 | 9/2018 | Pinchuk |
| 2018/0263752 A1 | 9/2018 | Pinchuk |
| 2018/0289464 A1 | 10/2018 | Kassab |
| 2018/0333563 A1 | 11/2018 | Agah |
| 2019/0046157 A1 | 2/2019 | Unser |
| 2019/0083705 A1 | 3/2019 | Allen |
| 2020/0038586 A1 | 2/2020 | Chomas et al. |
| 2020/0078555 A1 | 3/2020 | Agah |
| 2020/0108239 A1 | 4/2020 | Arepally et al. |
| 2020/0205840 A1 | 7/2020 | Adawi |
| 2020/0261695 A1 | 8/2020 | Jaroch et al. |
| 2020/0383688 A1 | 12/2020 | Olson |
| 2021/0244473 A1 | 8/2021 | Cook |
| 2021/0338976 A1 | 11/2021 | Jaroch et al. |

FOREIGN PATENT DOCUMENTS

| | | | |
|---|---|---|---|
| CN | 203107204 | U | 8/2013 |
| CN | 105007973 | A | 10/2015 |
| CN | 105208946 | A | 12/2015 |
| DE | 8910603 | U1 | 12/1989 |
| EP | 0416662 | B1 | 3/1991 |
| EP | 0533511 | A1 | 3/1993 |
| EP | 0554579 | A1 | 8/1993 |
| EP | 1226795 | | 7/2002 |
| EP | 1527740 | | 5/2005 |
| EP | 1743524 | A1 | 1/2007 |
| EP | 1803423 | | 7/2007 |
| EP | 2359893 | A1 | 8/2011 |
| EP | 3458136 | B1 | 3/2019 |
| FR | 2652267 | A1 | 3/1991 |
| GB | 2020557 | B | 11/1979 |
| JP | 2006051144 | A | 2/2006 |
| JP | 2006523515 | | 10/2006 |
| WO | 8905667 | | 6/1989 |
| WO | 9902093 | A1 | 1/1999 |
| WO | 199916382 | | 4/1999 |
| WO | 199944510 | A1 | 9/1999 |
| WO | 200141679 | | 6/2001 |
| WO | 200145592 | | 6/2001 |
| WO | 200149215 | A2 | 7/2001 |
| WO | 0197879 | | 12/2001 |
| WO | 02055146 | A1 | 7/2002 |
| WO | 2004043293 | | 5/2004 |
| WO | 2004075776 | | 9/2004 |
| WO | 2011068924 | | 6/2011 |
| WO | 2016149653 | | 9/2016 |
| WO | 2019140381 | A1 | 7/2019 |

OTHER PUBLICATIONS

"Allogenic Chimeric Antigen Receptor-Modified Cells for Adoptive Cell Therapy of Cancer", Marcus, Assaf et al., Mar. 24, 2014, Expert Opinion of Biological Therapy, vol. 14, Issue 7.
A Study of the Geometrical and Mechanical Properties of a Self-Expandig Metallic Stent Theory and Experiment, Dr. Michael R. Jedwab, Claude 0. Clerc, Journal of Applied Biomaterials, vol. 4, Issue 1, pp. 77-85, Spring 1993.
U.S. Appl. No. 61/266,068, filed Dec. 2, 2009, Chomas et al.
U.S. Appl. No. 61/382,290, filed Sep. 13, 2010, Chomas et al.
Cannulation of the Cardiac Lymphatic Sytem in Swine, Vazquez-Jiminez et al., European Journal of Cardio-thoracic Surgery 18 (2000) 223-232.
Catheter-Based Renal Sympathetic Denervation for Resistant Hypertension: a Multicentre Safety and Proof-of-Principle Cohort Study, Krum et al., The Lancet, 2009.
Development of Repeatable Microcatheter Access Port for Intra-arterial Therapy of Liver Cancer, Yasushi Fukuoka et al., Cardiovasc Intervent Radiol (2019) 42:298-303.
Embolization II, Scientific Session 11, JVIR, Mar. 27, 2012.
Embolization procedure lowers levels of "hunger hormone," leads to weight loss, EurekAlert Public Release, Mar. 7, 2013.
Estimation of Tumor Interstitial Fluid Pressure (TIFP) Noninvasively, Long Lian Liu et al., PLOS ONE | DOI:10.1371/journal.pone. 0140892 Jul. 28, 2016.
Finite Element Stent Design, M. De Beule, R. Van Impe, P. Verdonck, B. Verhegghe, Computer Methods in Biomechanics and Biomedical Engineering, 2005.
First-in-Man Study of Left Gastric Artery Embolization for Weight Loss, Nicholas Kipshidze et al., ACC.13, E2056, UACC Mar. 12, 2013, vol. 61, Issue 10.
Fusion Drug Delivery System-Novel Catheter/Stent Design for Targeted Drug Delivery, Gerschwind & Barnett, Non-Published US provisional patent application filed Sep. 17, 2007.
International Search Report and Written Opinion of Application No. PCT/US16/23723 dated Sep. 2, 2016.
International Search Report and Written Opinion of Application No. PCT/US19/13482 dated Jun. 10, 2019.
International Search Report of PCT/US18/22171 dated Aug. 3, 2018.

(56) References Cited

OTHER PUBLICATIONS

Left Gastric Embolization Leads to Weight Loss, Bariatriac News, Owen Haskins, Dec. 4, 2013.
Long-Term Catheterization of the Intestinal Lymph Trunk and Collection of Lymph in Neonatal Pigs, Richard R. Uwiera et al., Journal of Visualized Experiments, Mar. 2016, 109, e53457.
Lymphaniography to Treat Postoperative Lymphatic Leakage: A Technical Review, Edward Wolfgang Lee, et al., Korean Journal of Radiology 15(6), Nov./Dec. 2014.
Radiologic Placement of Side-hole Catheter with Tip Fixation for Hepatic Arterial Infusion Chemotherapy, Toshihiro Tanaka et al., J Vasc Interv Radiol 2003: 14:63-68.
Renal Denervation as a Therapeutic Approach for Hypertension: Novel Implications for an Old Concept, Schlaich et al., Hypertension, Journal of the American Heart Association, 2009, 54:1195-1201.
Renal Sympathetic-Nerve Ablation for Uncontrolled Hypertension, Schlaich et al., The New England Journal of Medicine, 2009, pp. 932-934, Aug. 27, 2009.
RenovoCath(tm) RC120 The Future of Targeted Delivery, RenovoRx Inc., web brochure downloaded from Internet on Feb. 2, 2015.
Search Report and Written Opinion of Application No. PCT/US 19/54406 dated Jan. 6, 2020.
Superselective Retrograde Lymphatic Duct Embolization for Management of Postoperative Lymphatic Leak, Bulent Arslan et al., Diagn Interv Radiol 2017; 23:379-380.
EP Search Report and Written Opinion of Application No. EP19739019 dated Sep. 17, 2021.
Japanese Office Action dated Apr. 28, 2021 of Application No. 2020-082002.
Canadian Office Action 2 dated Jun. 3, 2022 of Application No. 3,139, 118.
International Search Report and Written Opinion of Application No. PCT/US2020/034626 dated Aug. 26, 2020.
Japanese Office Action dated May 10, 2022 of Application No. 2021-572025.
Chinese Office Action and Search Report dated Jan. 10, 2022 of Application No. 201980016342.3.
U.S. Appl. No. 15/871,326, filed Jan. 15, 2018, Arepally et al.
U.S. Appl. No. 17/375,779, filed Jul. 14, 2021, Arepally et al.
U.S. Appl. No. 17/671,296, filed Feb. 14, 2022, Arepally et al.

\* cited by examiner

METHOD OF DELIVERING A THERAPEUTIC AGENT TO A SOLID TUMOR FOR TREATMENT

CROSS-REFERENCE TO RELATED APPLICATIONS

This application is a continuation of U.S. Ser. No. 16/219,738, filed Dec. 13, 2018, which is a divisional of U.S. Ser. No. 15/064,158, filed Mar. 8, 2016, which claims priority under 35 U.S.C. § 119(e) to U.S. provisional application Ser. No. 62/140,651, filed Mar. 31, 2015, the entire contents of which are hereby incorporated herein by reference.

BACKGROUND OF THE INVENTION

1. Field of the Invention

The present invention relates devices and methods for administering immunotherapy to a patient, particularly for the treatment of patients with solid tumors.

2. State of the Art

For many years the basic treatment for cancer has consisted of surgery, chemotherapy and radiation therapy. More recently, drugs that target cancer cells, such as imatinib (Gleevac®) and trastuzumab (Herceptin®) by guiding themselves to specific molecular changes seen in the cancer cells have also become standard treatments for a number of cancers.

Now, therapies that take advantage of a patient's immune system to fight their cancers are in clinical use or in development and gaining interest. There are four basic versions of immunotherapy products today, which can be used alone or in combination. These immunotherapy products include immunomodulators, vaccines, modified cells and check-point inhibitors.

Immunomodulators include IL-2, IL-7, IL-12, Interferons, G-CSF, Imiquimod, CCL3, CCL26, CXCL7, cytosine phosphate-guanosine, oligodeoxynucleotides, and glucans, and all operate to systemically increase the patient's immune response. Vaccines comprise an infusion of antigen directly or antigen-activated dendritic cells, which activate the patients white blood cells. Modified cells are blood-derived immune cells from the patient which are engineered and incubated to grow to a large number of modified cells that specifically target a region of tumor. This approach, referred to as adoptive cell transfer (ACT) has generated remarkable responses in the small clinical trials in which it has been investigated. Check-point inhibitors include anti-PD-1, which block the patient's natural suppression of T-cells, thereby effectively increasing the time and number of T-cells that can fight the cancer.

Immunotherapy practice has had success in "liquid" tumors, such as leukemia, where the therapy is easily delivered to the site of the cancer via intravenous injection or infusion. Further, immunotherapy has promise for solid tumors. However, delivery of the therapy with sufficient penetration into the tumors to allow the therapy to interact with the cancer cells remains a challenge.

In current practice, the immunotherapy agents are delivered by oral dosage, venous delivery, or catheter-based delivery to an organ of interest with a traditional microcatheter.

In venous delivery, the agent is generally infused into the patient through a peripherally inserted central catheter (PICC) or a port implanted in the patient. PICCs and ports can remain in place for several weeks or months and are used to reduce the number of times that a patient is subject to needle sticks and to reduce risk of tissue and muscle damage that can occur with a standard IV. While a PICC or port may be suitable for infusion of a chemotherapy treatment agent, which is generally circulated throughout the patient's circulation system, or for a "liquid" tumor, it may not be suitable for delivery of the immunotherapy agent to a solid tumor.

Microcatheters can be delivered to localize delivery of the agent to the vascular system adjacent the organ of interest. However, various issues prevent desirable agent uptake at the tumor.

SUMMARY

In accord with the invention, systems and methods are provided for delivery of immunotherapy agents to a solid tumor.

Solid tumors undergo angiogenesis, which creates unique vascular characteristics compared to healthy tissue. Solid tumors often have regions of high vascular density, a reduced resistance to flow, and a high capacitance for therapy. As a result of the unregulated tumor angiogenic process, a dense branching network of vessels is formed in the tumor. The formed dense network has a different vessel structure than health vessels. A healthy vessel is encased in endothelium, which maintains vascular tone and provides resistance to flow. Tumor vessels have a deteriorated endothelium and lack tone; this results in lower resistance to flow. Also, the dense network of vessels creates a relatively large vascular volume for the relative volume of the tissue, permitting a significantly higher volume of therapy to be deposited in the tumor compared to healthy tissue. Further, solid tumors can exhibit regions of low pressure within their vessels where there is robust flow, and they can have regions of high pressure where the vessels have become leaky and there is poor to no endogenous arterial flow. For these reasons, it is important to have an infusion system that does not rely solely on endogenous arterial flow to control delivery.

In view of these identified factors, it is believed by the inventors that immunotherapy systems and procedures should achieve several goals. Highly targeted delivery to the organ of interest should be obtained without the chance of back-flow into non-target regions. There should be the ability to increase pressure during infusion to overcome regions of high pressure in the tumor. More therapy should be deposited in the tumor than in the healthy tissue. The immunotherapy dose should deliver a maximum amount of intact cells or antibodies (a maximum percentage of healthy immunotherapy dose), and a minimum amount of damaged, destroyed cells, or activated cells during infusion. In addition, it is desirable to have a catheter deliver a homogenous immunotherapy dose across a vessel, including across a vessel branching network.

In accord with these goals, an immunotherapy treatment is delivered through a fully or partially deployed intravascular pressure modulating anti-reflux catheter, such as a catheter with microvalve and filter or a balloon catheter.

Further, the anti-reflux catheter may have one or more additional attributes that are advantageous in the delivery of cancer treatments. By way of example, these attributes can include the following. The catheter has self-centering capability that provides homogeneous distribution of therapy in a downstream branching network of vessels. The catheter includes an anti-reflux capability that blocks the retrograde flow of therapy into proximal non-target vessels proximal to the catheter tip. The system allows forward flow at a reduced pressure when not infusing therapy to target regions of low vascular resistance (tumor) and high capacitance (tumor). The valve and filter or a fully deployed balloon allows the pressure to be increased during infusion, with the pressure being modulated by the physician. An increased pressure allows increased delivery to and penetration into regions of the tumor that are naturally subject to high pressure conditions. According to another aspect of the device, a coating can be provided to the hub and inner lumen of the catheter to inhibit T-cell activation. According to yet another aspect of the device, a coating or construct can be provided to the hub and inner lumen of the catheter that optimize the wall shear during delivery of the therapy. By optimizing the wall shear gradient, the T-cells are subject to reduced trauma and maintain integrity during delivery while preventing clumping of the cells.

In accord with the method described herein, the treatment catheter is used in a method of delivering an immunotherapy agent. The treatment includes infusion of immunotherapy cells, anti-bodies, and/or other biologics into the target organ, including a selected location within the target organ, while maintaining a high integrity of the cells of the immunotherapy dose.

A modified Seldinger technique is used to introduce the catheter into the patient. More particularly, the catheter is introduced into the femoral artery, and then advanced up the aorta to the celiac axis. The catheter is then advanced into the left gastric artery. From the left gastric artery, the distal end of the catheter is advanced to the target artery that feeds the target organ. The catheter is then deployed for organ targeting.

Then, the immunotherapy agent, including immunotherapy T-cells, is infused under pressure through the catheter and to the tumor. Infusion is continued until the prescribed dose of immunotherapy is completely infused. This can occur at sub-stasis, at stasis, or beyond stasis. At stasis, the immunotherapy can be infused without any reflux. Further, by either manually inflating the balloon of a balloon catheter to block flow past the balloon in the vessel, or by use of the dynamically adjustable anti-reflux infusion catheter with valve, the immunotherapy can be infused beyond stasis without concern that the immunotherapy will reflux back toward the vessels of non-target tissues and/or organs.

After the infusion of the immunotherapy agent, the anti-reflux catheter is removed from the patient, and an arterial closure device is used to close the arterial access point for the procedure.

DETAILED DESCRIPTION OF THE PREFERRED EMBODIMENTS

With reference to the human body and components of the devices and systems described herein which are intended to be hand-operated by a user, the terms "proximal" and "distal" are defined in reference to the user's hand, with the term "proximal" being closer to the user's hand, and the term "distal" being further from the user's hand, unless alternate definitions are specifically provided.

Methods are provided herein for infusing an immunotherapy agent to a tumor site for treatment of cancer. The method includes use of an infusion catheter device. In accord with the method, the infusion catheter device is an infusion microcatheter with valve and filter, or filter valve, (hereinafter "microvalve catheter") or an infusion microcatheter with a distal balloon (hereinafter "balloon catheter"), with both such devices collectively referred to herein as "anti-reflux infusion catheters". Whereas the balloon catheter is manually operable between expanded (open) and collapsed (closed) configurations, the microvalve catheter is a dynamic device, automatically moving between open and closed configurations based on local fluid pressure conditions to which the proximal and distal surfaces of the valve and filter are subject.

Figure 1A:
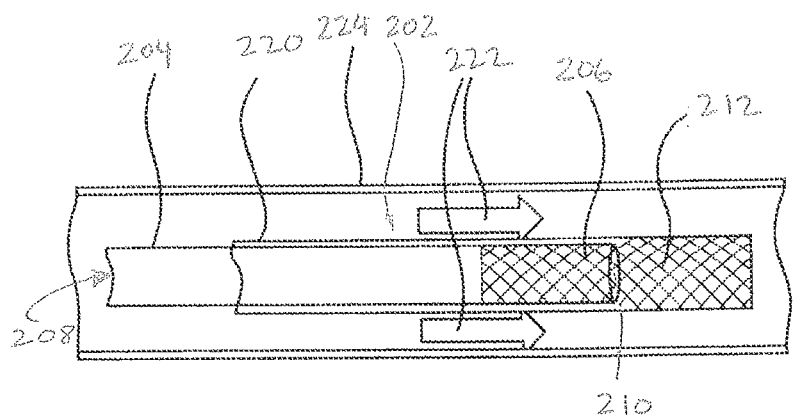
FIGS. 1A-1C are schematic diagrams of one exemplary embodiment of an apparatus of the invention respectively in an undeployed state, a deployed partially open state with blood passing in the distal direction, and a deployed fully open state where the blood flow is static.
Figure 1B:
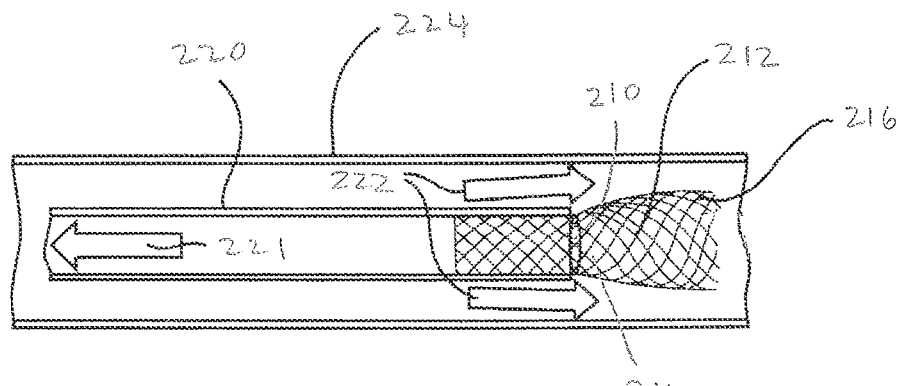
Figure 1C:
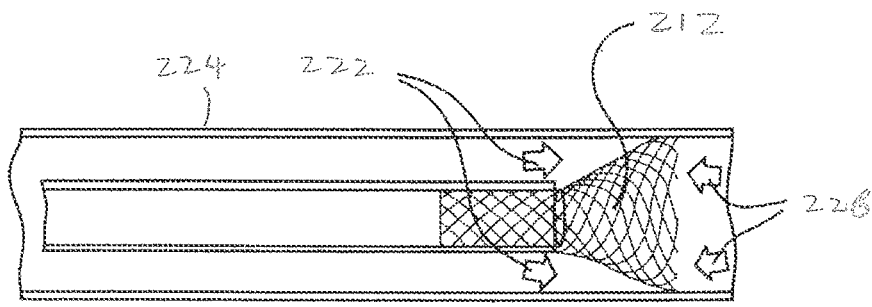

By way of example, referring to FIGS. 1A through 1C, an embodiment of an anti-reflux catheter 202 includes a flexible microcatheter 204 having a proximal end (not shown) and a distal end 206. A lumen 208 extends through the microcatheter and has a distal orifice 210, preferably coaxial with the axis of the catheter. A filter valve 212 is attached to the distal end 206 of the microcatheter, such that the orifice 210 opens into the proximal end 214 of the filter valve 212. The filter valve 212 comprises a braided polymeric filamentary structure 216 that is adapted to dynamically open and close based on the relatively proximal and distal pressure conditions of the fluid to which the filter valve is subject within a vessel 224. At least a portion of the braided filamentary structure 216 includes a polymeric filter 218 thereon, preferably deposited by electrospinning or electrostatic deposition to bond with the braided filamentary structure (FIGS. 1A and 2B). The filter 218 has a pore size not exceeding 500 μm. With such pore size, the filter 218 construct is semi-porous and allows elevated pressure differentials (greater distal pressure) to dissipate. The microcatheter 204 is adapted for use with an outer delivery catheter 220, with the inner microcatheter 204 extending through the outer delivery catheter 220. Longitudinal displacement of the outer catheter relative to the inner catheter (in the direction of arrow 221) allows the filter valve 212 to move from a non-deployed configuration (FIG. 1A) to a deployed configuration (FIG. 1B). Once deployed, the filter valve 212 is adapted to dynamically move between open and closed configurations (FIG. 1B to FIG. 1C and back) based upon fluid pressure forces 222, 226 applied to the proximal and distal sides of the filter valve when the device 202 is deployed within a vessel 224 (FIG. 1C). Such a microvalve catheter is disclosed in detail in incorporated U.S. Pat. Nos. 8,500,775 and 8,696,698 and in 9,968,740. In addition, microvalve catheters structurally and functionally similar to that described are sold by Surefire Medical, Inc., Westminster, Colorado, as part of the Surefire Infusion System.

Figure 3A:
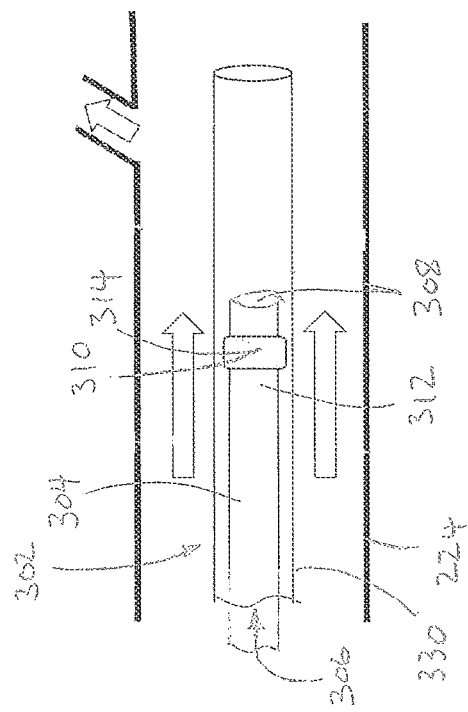
FIGS. 3A-3C are schematic diagrams of another exemplary embodiment of an apparatus of the invention respectively in an undeployed state, a deployed partially open state with blood passing in the distal direction, and a deployed fully open state where the blood flow is static.
Figure 3C:
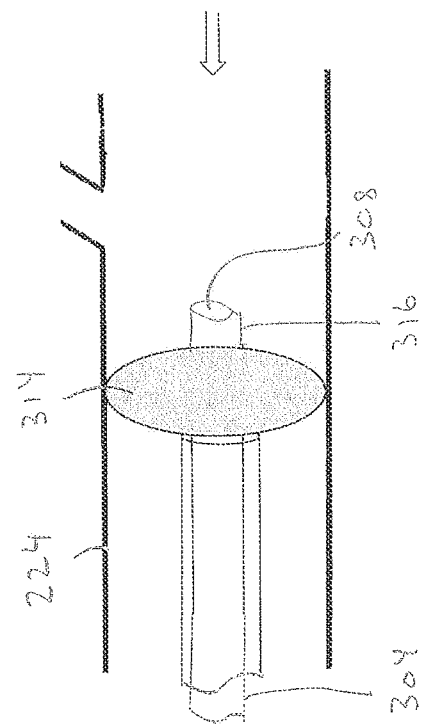
Figure 3B:
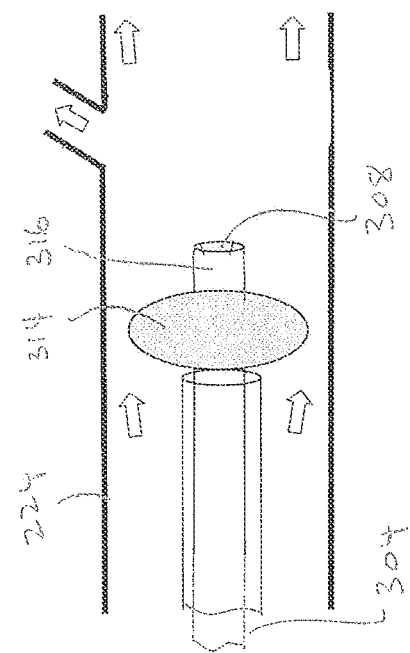

Turning now to FIGS. 3A through 3C, as another example, another microvalve catheter 302 includes a catheter 304 having a first lumen 306 for infusing the embolizing agent out of a distal orifice 308, and a second inflation lumen (not shown). An elastic membrane 310 is provided about a distal portion 312 of the catheter 304 and has a lower surface in communication with the inflation lumen to define a fluid inflatable balloon 314. FIG. 3A shows the balloon 314 in a collapsed configuration, FIG. 3B shows the balloon 314 in a partially expanded configuration (i.e., expanded insufficiently to reach across the vessel walls 224), and FIG. 3C shows the balloon 314 in a fully expanded configuration (i.e., expanded fully to the vessel walls 224). It is preferred that the balloon 314 be proximally offset from the distal tip 316 of the catheter 304 and particularly the orifice 308 of the first lumen. The balloon catheter device 302 may additionally include multiple balloons, optionally of different sizes, and either radially or longitudinally offset. The balloon is preferably provided for use with an outer delivery catheter 330, as discussed below.

In accord with one preferred aspect of the anti-reflux infusion catheter used in the method, the anti-reflux infusion catheter is adapted to self-center within a vessel 224. This can be accomplished with the expandable balloon 314 being centered about the balloon catheter, or the expandable valve 212 (FIGS. 1B and 1C) expanding radially symmetrically about the catheter. The self-centering of the anti-reflux infusion catheter is effected to promote homogeneous distribution of immunotherapy in a downstream branching network of vessels. That is, in distinction from a single streamline of delivery from a prior art end-hole catheter, a centrally-positioned anti-reflux infusion catheter creates turbulent flow in a vessel to mix the infused immunotherapy evenly across the cross-sectional area of a vessel.

In accord with another preferred aspect of the anti-reflux infusion catheter, such catheter blocks retrograde flow of immunotherapy into proximal non-target vessels proximal to the catheter tip, or a balloon or a valve on the catheter. In accord with yet another aspect of the anti-reflux infusion catheter, the valve and filter or a partially deployed balloon permit forward flow at a reduced pressure when not infusing the immunotherapy to target regions of low vascular resistance (tumor) and high capacitance (tumor).

Figure 4:
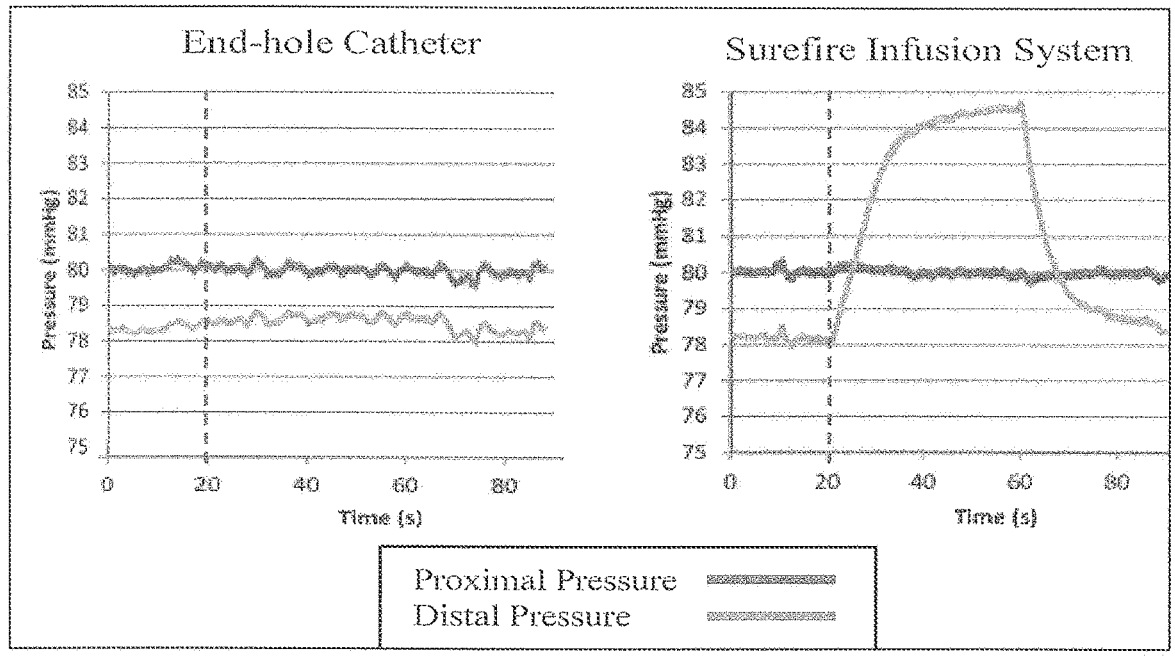
FIG. 4 is a graph showing the performance of the apparatus of FIGS. 1A-1C compared to the performance of a prior art end-hole catheter in delivering immunotherapy agent under pressure to target tissue.

In accord with yet another aspect of the anti-reflux infusion catheter, the valve and filter or a fully deployed balloon allows the infusion pressure to be increased during infusion, with the pressure being modulatable by the physician. By increasing the pressure, an increase in delivery and penetration of the immunotherapy into regions of the tumor that are naturally subject to high pressure conditions is effected. Referring to FIG. 4, it is seen that a microvalve anti-reflux catheter of the type available from Surefire Medical, Inc. allows infusion to generate substantially elevated distal pressures relative to a prior art end-hole catheter (with no anti-reflux structure or function). The pressure applied by the Surefire device dissipated after infusion, as fluid was able to diffuse back through the semi-porous membrane of the valve and filter. The end-hole catheter was unable to generate pressure gradients distal to the tip during infusion as fluid was able to reflux, equalizing fluid pressure in the system.

In accord with another aspect of the anti-reflux catheter (with reference to device 202, but equally applicable to device 302), an inner lining of the lumen 208 of the catheter 204 is tailored to minimize surface energy and interaction with T-cells. The inner lining of the lumen 208 is coated with one or more polymers 230 (FIG. 2A) such as silicones and silicone oils, polypropylene, polyethylene and fluoropolymers such as polytetrafluoroethylene, polyvinylidene fluoride, fluorinated ethylene-propylene, and perfluorinated elastomers.

Figure 2A:
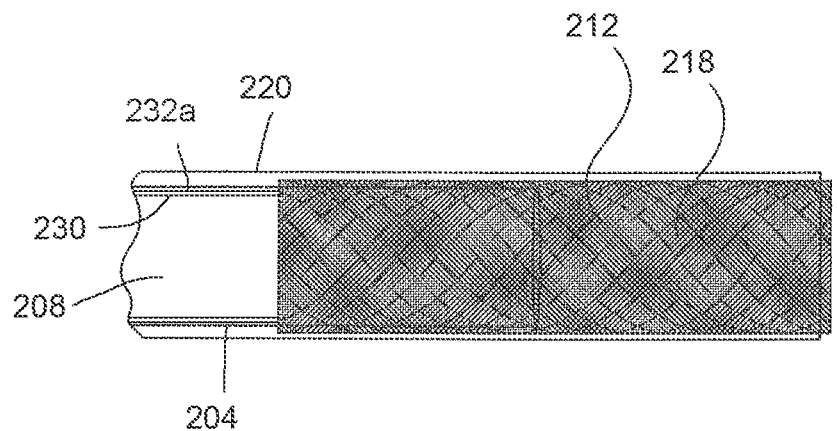
FIGS. 2A-2B are schematic diagrams of an exemplary embodiment of a valve having a braid component that is covered by a filter component in respectively an undeployed state and a deployed state.
Figure 2B:
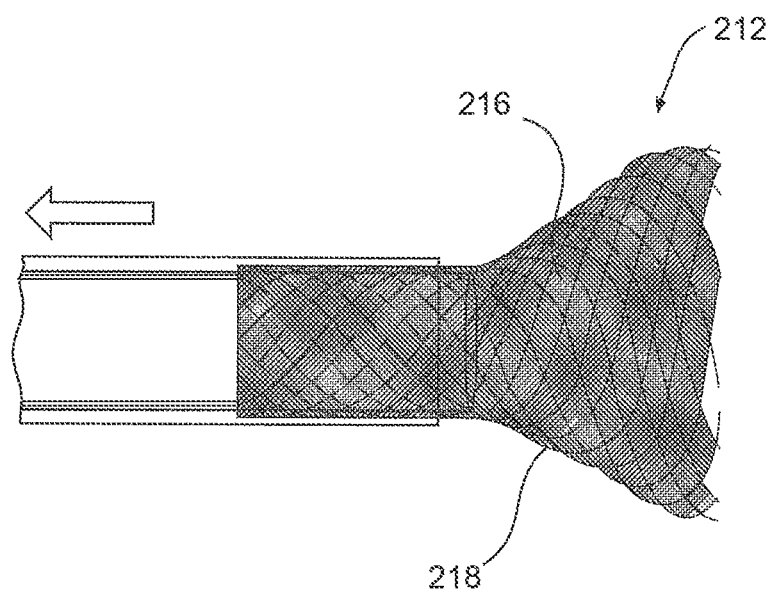
Figure 5:
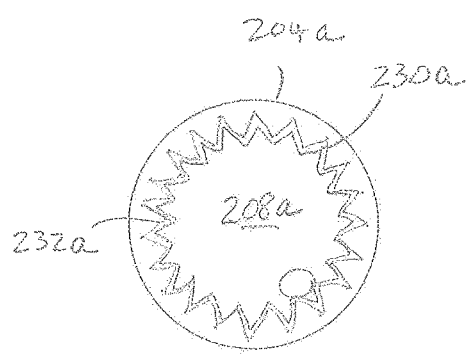
FIG. 5 is a schematic cross-sectional view across an embodiment of the anti-reflux catheter including oleophobic and/or a hydrophobic surface geometry (shown not to scale).

In accord with another aspect of the anti-reflux catheter, as an addition to or alternative to the coating described above, an inner lining surface 232a of the lumen 208a of the catheter 204a is structurally patterned to create an oleophobic and/or a hydrophobic surface geometry (FIGS. 2A and 5). In accord with such aspect, the inner lining surface 232a can be patterned to include micro and/or nano scale ridges, pillars, or other features that generate a rough hydrophobic surface. Such features may be further chemically modified with fluoropolymers 230a (such as perfluoropolyether), silicones, or other chemical entities to enhance the hydrophobic effect and/or to provide oleophobic functionality to the surface features.

In accord with another aspect of the anti-reflux catheter, as an addition to or alternative to the coatings and structure described above, the inner lining surface of the lumen can be modified with hydrogels that can act to inhibit T-cell attachment and/or activation or can be used as protectants against fluid-mechanical cell damage. Such polymers are typically hydrophilic and electrically neutral and hydrogen bond acceptors rather than hydrogen bond donors. Examples include but are not limited to polyvinyl alcohol (PVA) and chemically modified PEO-(X) hybrid gels, poly(ethylene) glycol (PEG) and chemically modified PEG-(X) hybrid gels (PEGylated polymers), polyethylene oxide (PEO) and chemically modified PEO-(X) hybrid gels, Poly(acrylic acid), 2-hydroxyethyl methacrylate (HEMA)-based polymers and zwitterionic hydrogels such as phosphobetaine, sulfobetaine, and carboxybetaine which can display variable surface activity based on environmental pH. Furthermore, natural or artificial protein layers can be provided to the lumen surface or the hydrogel network and can have specific cellular stabilizing activities. Such a protein layer can include cytokines. Such polymers and proteins can be attached in cross-linked networks or in "brushy" layers of polymer strands. Methodology includes self-assembled monolayers of short chain hydrogels or peptides attached to the inner surface of the lumen of the catheter using a variety of covalent or ionic bonding chemistry and layer-by-layer self-assembly of tailored functionality nano-composite gels.

In accord with another aspect of the anti-reflux infusion catheter, an alternative or additional coating or structure can be provided to the hub and/or inner lining of the lumen of the catheter that will reduce the wall shear stress during delivery of the immunotherapy. Such a coating or structure can include a hydrophilic coating, a hydrophobic coating, or a small 'brushy' fibrous layer that acts to create a region of low flow or no flow along the wall of the catheter. By way of example, the coating can include glycocalyx or a glycocalyx-mimicking layer. Glycocalyx is a glycoprotein-polysaccharide, including several carbohydrate moieties of membrane glycolipids and glycoproteins. In the vascular endothelial tissue, the glycocalyx is a small, irregularly shaped layer extending approximately 50-100 nm into the lumen of a blood vessel, but can be up to 11 μm thick. The coating in the lumen can mimic such biological structure.

Figure 6:
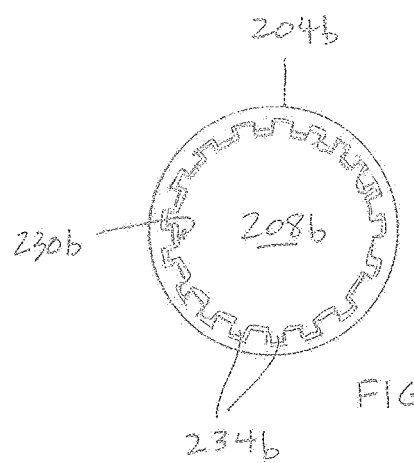
FIG. 6 is a schematic cross-sectional view across an embodiment of the anti-reflux catheter including a surface geometry that minimizes wall shear (shown not to scale).

In accord with another aspect of the anti-reflux infusion catheter, wall shear stress along the lumen can be modified by incorporating a surfactant coating 230b into the lining of the lumen of the catheter. By way of another example, the wall shear stress can be modified by extruding the lumen 208b of the catheter 204b with features, including elongate channels 234b formed along length and open to the central lumen 208b (FIG. 6). Such channels 234b are either smaller or bigger than the diameter of a T-cell (e.g., less than 7 microns across or greater than 20 microns across) so as to prevent the channels from engaging and filling with captured T-cells. Thus, the channels will fill with fluid, but no T cells, and the peripheral channel-fluid will guide passage and minimize wall shear stress of the T cells through the lumen.

By way of another example, the catheter is negatively charged. In one manner, this can be effected by providing wires or even a braid about the lumen and applying a negative voltage to the wires (with no/negligible current during use); in another manner, the catheter is constructed with a negatively charged polymer. The immunotherapy agent is naturally negatively charge (as T-cells have negative surface charge). Then, the T-cells in the immunotherapy agent are repelled from the lumen surface to thereby reduce the shear stress upon infusion of the immunotherapy agent.

In accord with another manner of reducing wall shear stress, the wall shear stress can be minimized by incorporating a surfactant into the immunotherapy fluid containing the T cells. The surfactant can be premixed with the immunotherapy agent or mixed at the time of infusion.

In accord with a preferred procedure for delivering immunotherapy, a modified Seldinger technique is utilized. In the Seldinger technique, which is well-known and will not be described in detail herein, access is provided from the thigh to the femoral artery and a guidewire is advanced to the aorta. The delivery catheter is advanced over the guidewire. Once the delivery catheter is at its intended position, and in accord with the method herein, an anti-reflux infusion catheter is advanced through the delivery catheter and over the guidewire.

Then the anti-reflux catheter is displaced relative to the delivery catheter to expose the distal end of the anti-reflux catheter. The anti-reflux catheter is deployed.

Then, the immunotherapy agent, including immunotherapy T-cells, is infused through the catheter and under pressure to the tumor. Infusion is continued until the prescribed dose of immunotherapy is completely infused. This can occur at sub-stasis, at stasis, or beyond stasis. At stasis, the immunotherapy can be infused without any reflux. Further, by either manually inflating the balloon of a balloon catheter to block flow past the balloon in the vessel, or by use of the dynamically adjustable anti-reflux infusion catheter with valve, the immunotherapy can be infused beyond stasis without concern that the immunotherapy will reflux back toward the vessels of non-target tissues and/or organs.

After the infusion of the immunotherapy agent, the anti-reflux catheter is removed from the patient, and an arterial closure device is used to close the arterial access point for the procedure.

There have been described and illustrated herein embodiments of apparatus and methods for delivering immunotherapy agents to target tissue. While particular embodiments of the invention have been described, it is not intended that the invention be limited thereto, as it is intended that the invention be as broad in scope as the art will allow and that the specification be read likewise. Particularly, it is intended that various aspects presented with respect to coated and structurally modifying the lining of the lumen described herein can be used either alone, or in combination with one or multiple other aspects. To such extent, it is anticipated that the lumen can include both structural modification and/or multiple coatings to facilitate passage of the immunotherapy with the least negative effect on the T-cells in the therapy. It will therefore be appreciated by those skilled in the art that yet other modifications could be made to the provided invention without deviating from its spirit and scope as claimed.

What is claimed is:

1. A method of delivering a therapeutic agent through a target vessel in communication with a tumor, the method comprising:
   a) inserting a delivery device into the target vessel, the delivery device comprising a flexible catheter having a proximal end and a distal end, an expandable fluid pressure modulating structure fixed adjacent the distal end of the flexible catheter, an agent delivery lumen extending through the flexible catheter from the proximal end of the flexible catheter to the distal end of the flexible catheter and opening to an orifice at a distal tip of the flexible catheter, wherein the agent delivery lumen is coated or structured to be hydrophobic and is coated or structured to reduce wall shear stress during infusion;
   b) deploying the expandable fluid pressure modulating structure in the target vessel to generate turbulent flow within the target vessel distal to the expandable fluid pressure modulating structure; and
   c) infusing the therapeutic agent through the agent delivery lumen, out of the orifice of the flexible catheter, and into the turbulent flow generated within the target vessel, while the expandable fluid modulating structure blocks retrograde flow of the therapeutic agent proximal of the expandable fluid pressure modulating structure.

2. The method of claim 1,
   wherein the therapeutic agent comprises an immunotherapy agent.

3. The method of claim 2,
   wherein the agent delivery lumen is coated and structured to be hydrophobic.

4. The method of claim 2,
   wherein the therapeutic agent comprises immunotherapy cells.

5. The method of claim 2,
   wherein the therapeutic agent comprises an immunomodulator.

6. The method of claim 5,
   wherein the immunomodulator is a cytosine phosphate-guanosine oligodeoxynucleotide.

7. The method of claim 1,
   wherein the expandable fluid pressure modulating structure is a microvalve configured to dynamically move between open and closed configurations responsive to fluid pressure conditions within the target vessel.

8. The method of claim 1,
   wherein the coating of the agent delivery lumen is selected from the group consisting of silicones and silicone oils, polypropylene, polyethylene and fluoropolymers.

9. The method of claim 1,
   wherein the delivery device further comprises an outer catheter, the flexible catheter extending through the outer catheter, and the outer catheter being longitudinally displaceable relative to the flexible catheter; and wherein the expandable fluid pressure modulating structure is deployed by longitudinally displacing the outer catheter relative to the flexible catheter.

10. The method of claim 1, wherein the agent delivery lumen comprises a structure comprising at least one feature selected from the group consisting of micro or nano scale ridges, or pillars.

11. The method of claim 1, wherein the agent delivery lumen is coated or structured to prevent engaging with the therapeutic agent during infusion.

* * * * *